United States Patent [19]
Tang et al.

[11] Patent Number: 5,729,583
[45] Date of Patent: Mar. 17, 1998

[54] MINIATURE X-RAY SOURCE

[75] Inventors: Cha-Mei Tang, Potomac; Richard D. Deslattes, Rockville, both of Md.

[73] Assignee: The United States of America as represented by the Secretary of Commerce, Washington, D.C.

[21] Appl. No.: 536,364

[22] Filed: Sep. 29, 1995

[51] Int. Cl.$^6$ ..................................................... H01J 35/06
[52] U.S. Cl. .......................... 378/122; 378/136; 378/138
[58] Field of Search ..................................... 378/136, 119, 378/121, 122, 138, 143, 64, 65

[56] References Cited

U.S. PATENT DOCUMENTS

| | | | |
|---|---|---|---|
| Re. 34,421 | 10/1993 | Parker et al. | 378/121 |
| 4,670,894 | 6/1987 | Birnbach et al. | 378/122 |
| 5,014,289 | 5/1991 | Rothe | 378/136 X |
| 5,030,921 | 7/1991 | Kane | 330/70 |
| 5,142,652 | 8/1992 | Reichehberger et al. | 378/136 |
| 5,153,900 | 10/1992 | Nomikos et al. | 378/65 |
| 5,165,093 | 11/1992 | Miller | 378/138 |
| 5,192,240 | 3/1993 | Komatsu | 445/24 |
| 5,229,682 | 7/1993 | Komatsu | 313/309 |
| 5,259,014 | 11/1993 | Brettschneider | 378/136 X |
| 5,428,658 | 6/1995 | Oettinger et al. | 378/136 X |

FOREIGN PATENT DOCUMENTS

| | | | |
|---|---|---|---|
| 2339225 | 3/1974 | Germany | 378/122 |

OTHER PUBLICATIONS

Tang, Cha-Me, *Microelectonic Cathodes for RF Sources & Accelerators Applications*, IEE Particle Accelerator Conf., Dallas, May 1995.

Bandy, et al. *Single–Crystal Monolithic Three–Terminal Vacuum Microelectronic Devices Having Maximum Stable Gain at One GH_z*, (Varian Ginzton Research Center, Palo Alto, CA 94304). No date.

Hsu, David S.Y. & Gray, Henry. *Vertical Thin–Film–Edge Field Emitters Fabricated by Chemical Beam Deposition* (Naval Research Laboratory, Washington, DC 20375). No date.

Auciello, M.A., et al. *Low Voltage Electron Emission from $Pb(Zr_x ni_{1-x})o3$–Based Thin Film Cathodes*, (MCNC, Electronics Technology Division, Research Triangle Park, NC 27709) No date.

Akinwande, A.I., et al., *Thin–Film–Edge Emitter Vacuum Micro–electronics Devices for Lamp/Backlight Applications*, (MIT, Cambridge, MA and Honeywell Technology, Plymouth, MN) No date.

Sadwick, L.P., et al., *Microminiature Thermionic Vacuum Tube Diodes*, (University of Utah, Dept. of Electrical Engineering). No date.

Sadwick, L.P., et al. *Progress in Microminiature Thermionic Vacuum Tube Devices*, IEEE Technical Digest of 1994, Int'l Elecronic Devices Meeting. No date.

Spindt, C.E., et al. *Field Emitter Arrays for Vacuum Micro–Electronics*, (SRI International, Menlo Park, CA) No date.

*Primary Examiner*—David P. Porta
*Attorney, Agent, or Firm*—Leydig, Voit & Mayer, Ltd.

[57] ABSTRACT

An x-ray head according to the invention includes an evacuated chamber in which a cathode and an anode are disposed and electrical connections from the anode and cathode extending through the wall of the evacuated chamber. The cathode may include a gated array of field emission elements, an array of solid state miniature thermionic cathodes, or ferroelectric cathodes. The anode is a metal producing x-ray radiation in response to the impact of electrons produced by the cathode. The anode may be a foil, a thin film of metal deposited on the inside surface of a wall of the evacuated chamber, or a self-supporting body of a metal that produces x-rays in response to electron impacts. The wiring may include conventional pins penetrating through and sealed to the wall of the chamber for connection to a flexible cable.

12 Claims, 7 Drawing Sheets

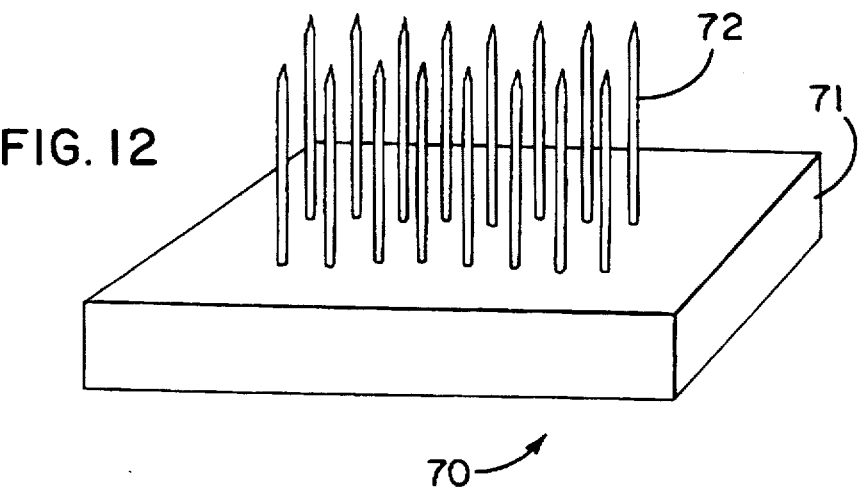
FIG. 12
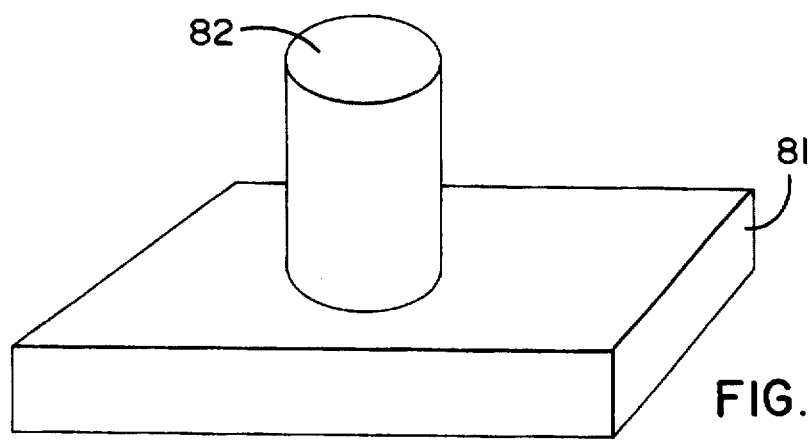
FIG. 13
FIG. 14(b)
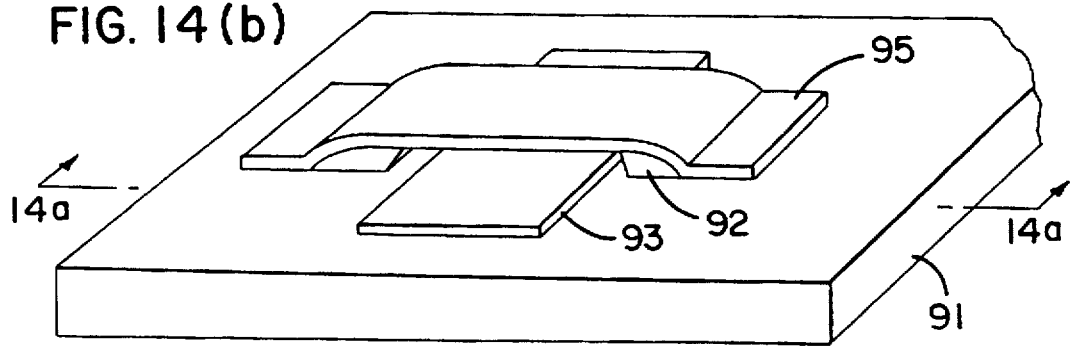

MINIATURE X-RAY SOURCE

FIELD OF THE INVENTION

The present invention relates to a miniature x-ray source for radiotherapy, diagnostic radiography, and laboratory radiography and, more particularly, to a miniature x-ray source.

BACKGROUND ART

X-ray radiation is used extensively by health care providers for diagnostic and treatment purposes. X-ray radiation is typically produced by high energy electrons generated and accelerated in a vacuum to impact on a refractory metal target. The intensity of x-ray radiation produced depends upon the magnitude of the electron current and the distribution of x-ray energies produced depends upon characteristics of the metal target and the energy of the electrons. The energy spectrum produced includes a continuous component spread across a relatively wide range of energies and characteristic peak energies that depend on the composition of the target.

Radiotherapy is a method of treatment in which a relatively high dose of x-rays, high energy charged particle beams, or gamma rays emitted by radioactive isotopes irradiate diseased and normal tissues. The irradiated cells are damaged and die or are unable to reproduce. By contrast, diagnostic radiography uses a relatively low dose of x-rays or other high energy waves or particles without significant biological damage to form an image on a photographic film or plate or on a fluoroscopic screen.

The goal of radiotherapy is to produce biological damage of a controlled volume of tissue, e.g., a tumor, while avoiding damaging adjacent normal tissues. In order to concentrate a beam of electromagnetic radiation from a conventional source on a particular region within a patient, the patient may be moved relative to the beam so that the controlled volume is continuously irradiated and adjacent normal tissues are irradiated only part of the time. When the source of treating radiation is a radioisotope, it may be placed directly within or adjacent the volume of tissue to be treated and the irradiation of adjacent normal tissue is limited.

Although radioisotopes provide certain advantages over conventional x-ray sources in controlled treatment of abnormal tissues, particular care is required in using, storing, and disposing of radioactive materials used in these processes to avoid undue risks to health care personnel and the environment. Moreover, regulatory requirements for documenting the use, custody, and disposal of radioactive materials are onerous, making their use undesirable.

A miniature x-ray source that avoids use of radioisotopes but allows localized application of radiation without measures such as relative movement of patient and x-ray sources is described in U.S. Reissue Patent 34,421 to Parker et al. The description of the Parker reissue patent is incorporated by reference. That x-ray source includes a glass envelope enclosing an anode with a tungsten target and a cathode for producing electrons for bombarding the target. The Parker x-ray source employing a heated thermionic cathode employs an anode for collecting an electron current and generating x-rays without any intermediate control element, such as a grid. Parker also describes an alternative field emission cathode in which a pointed element has electrons extracted from it by a high intensity electric field produced by a voltage difference between the anode of the x-ray source and the field emission cathode.

SUMMARY OF THE INVENTION

The present invention is directed to a miniature x-ray source including an x-ray head. An x-ray head according to the invention includes an evacuated chamber in which a cathode and an anode are disposed and electrical connections from the anode and cathode extending through the wall of the evacuated chamber. The cathode may include a gated array of field emission elements, an array of solid state miniature thermionic cathodes, or ferroelectric cathodes. The anode is a metal producing x-ray radiation in response to the impact of electrons produced by the cathode. The anode may be a foil, a thin film of metal deposited on the inside surface of a wall of the evacuated chamber, or a self-supporting body of a metal that produces x-rays in response to electron impacts. The wiring may include conventional pins penetrating through and sealed to the wall of the chamber for connection to a flexible cable.

A miniature x-ray source according to a first aspect of the present invention includes a gated field emission cathode producing electrons in response to an electric field and including a gate electrode for controlling the flow of electrons from the cathode to the anode.

A miniature x-ray source according to a second aspect of the present invention includes a thin film thermionic cathode including a metal film directly heated by a current flowing through the metal film for emitting electrons.

A miniature x-ray source according to a third aspect of the present invention includes a ferroelectric cathode producing electrons in response to a pulsed electrical signal.

A miniature x-ray source according to a fourth aspect of the present invention includes an envelope having a generally planar portion on which an anode is disposed and from which x-ray radiation is emitted and a collimating element disposed adjacent the planar portion of the envelope for collimating x-ray radiation produced at the anode.

BRIEF DESCRIPTION OF THE DRAWINGS

FIG. 12 is a perspective view of an ungated field emission cathode that may be used in embodiments of the invention.

FIG. 13 is a perspective view of an ungated field emission cathode that may be used in embodiments of the invention.

FIGS. 14(a) and 14(b) are, respectively, cross-sectional and perspective views of a thin film thermionic cathode that may be used in embodiments of the invention.

In all figures, like elements are given the same reference numbers.

DESCRIPTION OF THE PREFERRED EMBODIMENTS

Figure 1:
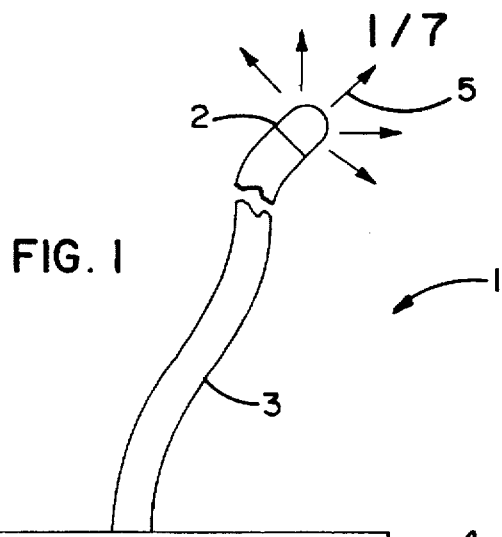
FIG. 1 is a schematic representation of a miniature x-ray apparatus according to the present invention.

FIG. 1 is a schematic representation of a miniature x-ray apparatus 1 according to one embodiment of the present invention. The miniature x-ray apparatus 1 comprises an x-ray source including a head 2, a flexible power cable 3 to which the head 2 is connected, and an electronic control and instrumentation system 4 including an internal power supply and connected to the cable 3. The x-ray head 2 includes a vacuum chamber, described below, that houses a microscopic cathode for generating electrons and an anode that accelerates and attracts the electrons and emits x-ray radiation 5 upon bombardment by the accelerated electrons. As described in detail below, numerous kinds of cathodes can be employed in the x-ray head 2. For example, among the cathodes that can be employed are a field emission cathode in which electrons are emitted in response to an intense electric field, a thermionic cathode from which electrons are produced in response to heat, and a ferroelectric cathode in which electrons are expelled in response to rapidly switched electrical pulses. The exterior of the x-ray head 2 is preferably covered with a thin, tough biocompatible plastic, particularly if the envelope of the vacuum chamber of the x-ray head 2 is glass, as preferred. An example of such a plastic is polytetrafluoroethylene.

In the following discussion, an x-ray head according to the invention is first described generically with regard to its structure. Then, numerous alternative embodiments providing various x-ray radiation patterns are described. Thereafter, different kinds of cathodes that may be employed in the generic x-ray head and the alternative structures producing various x-ray patterns are individually described.

Figure 2:
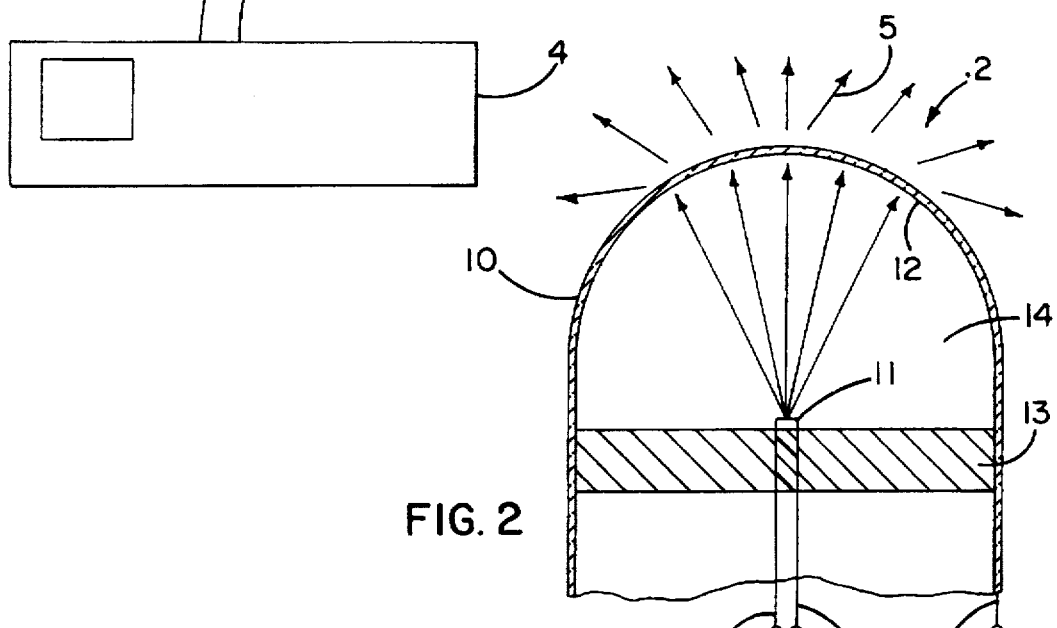
FIG. 2 is a schematic cross-sectional view of an x-ray head generally illustrating the principles of the invention.

FIG. 2 is a schematic, sectional side view of a generic x-ray head 2 that may be employed in the invention. The x-ray head includes a wall 10 of a material that is substantially transparent to x-rays and that can maintain the high vacuum required for production and transit of electrons from a cathode 11 within the evacuated volume of the x-ray head 2 to an anode 12 so that x-rays are produced. As illustrated in FIG. 2, the anode 12 may be a metal foil or a metal film deposited on the inside surface of the wall 10. However, other anode embodiments, as described below, can be used. Preferably, the wall 10 is a glass envelope that forms a closed volume, i.e., the vacuum chamber 14, in which the cathode 11 is disposed.

An electrically insulating supporting member 13 may form a wall of the evacuated chamber 14 or may merely provide a support for the cathode 11 with the center wall 10 being closed on itself, as shown in other figures. The insulator 13 is a conventional electrical insulator that can withstand relatively high temperatures, such as a glass, alumina, sapphire, or the like. Although not shown, an exhaust port is provided for evacuating the vacuum chamber 14 and the port is sealed, using conventional techniques, after the evacuation of the chamber 14 is complete. The cathode 11 includes at least one and usually two electrical connections 15 and 16 depending upon the particular cathode structure employed. Thermionic cathodes include at least three electrical connections. The anode 12 includes an electrical connection 17 to which the accelerating voltage, typically 10 to 60 Kv, is applied. All of the electrical connections are connected to respective conductors in the cable 3.

Figure 3A:
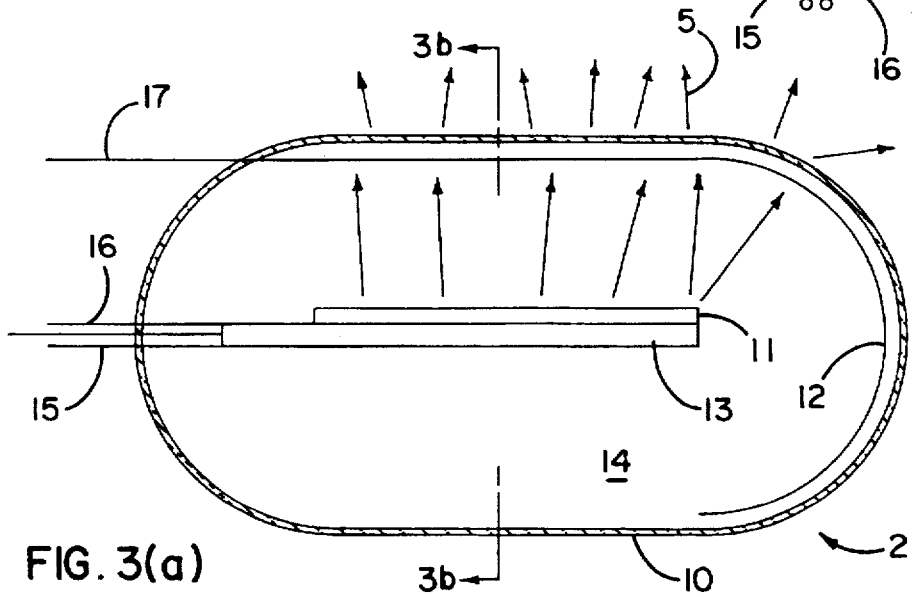
FIGS. 3(a) and 3(b) are, respectively, side and sectional views of an x-ray head according to an embodiment of the invention.
Figures 3B, 4A, 4B:
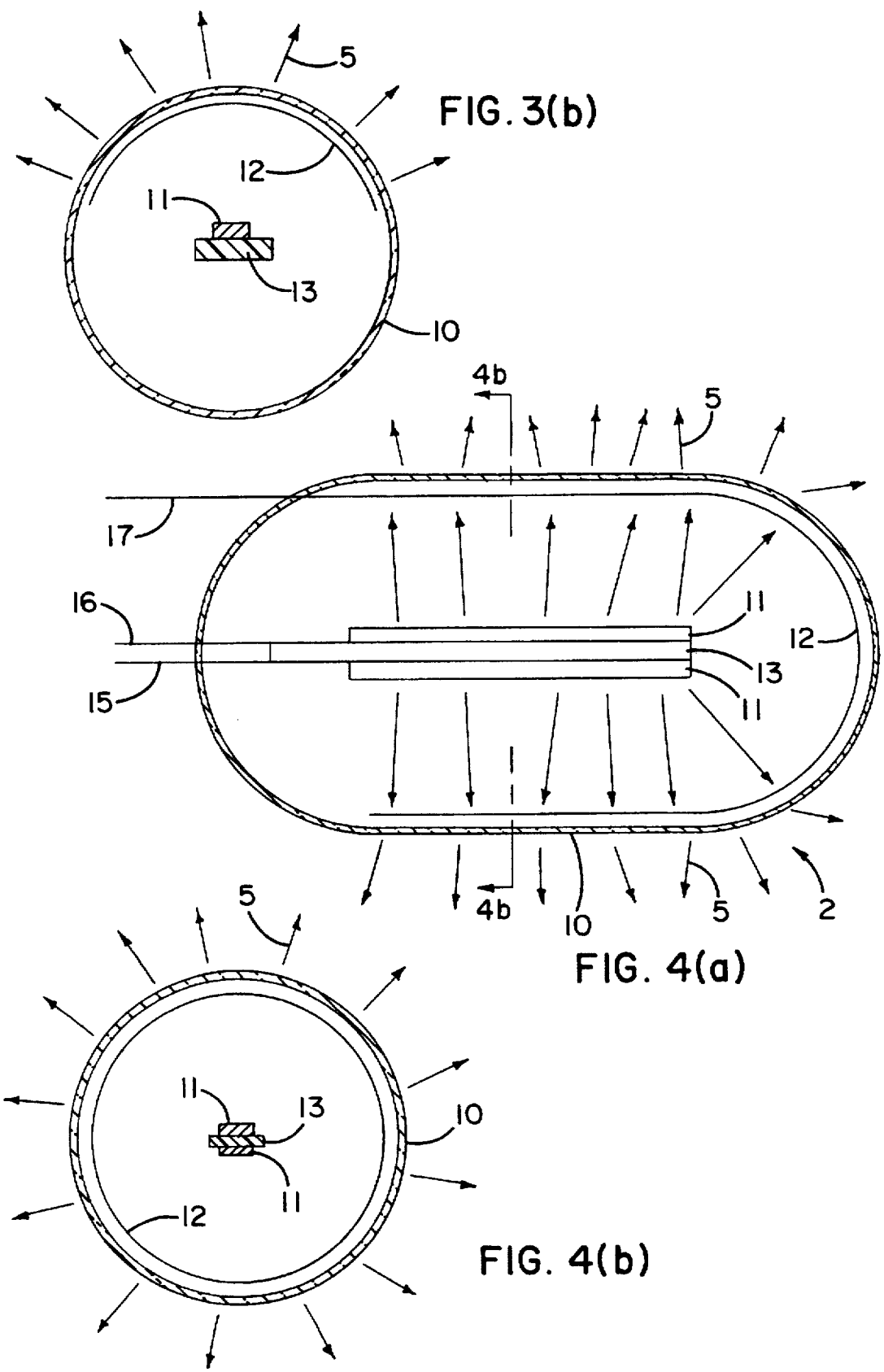
FIGS. 4(a) and 4(b) are, respectively, side and sectional views of an x-ray head according to an embodiment of the invention.

FIGS. 3(a), a schematic side view, and 3(b), a cross-sectional view, illustrate another x-ray head 2 according to an embodiment of the invention. FIG. 3(b) is a cross-sectional view taken along line 3b—3b of FIG. 3(a). In this embodiment, the outer wall of the vacuum chamber 14 is shown to be continuous and sealed to the leads, which may be bare, stiff metal pins, extending through the wall 10 for connection to the electrical cable 3. In the illustrated embodiment, the cathode 11 is supported on an insulating substrate 13 and includes three extending wires, for example, as are used in a thermionic cathode. The anode 12 is shown spaced from the wall 10 in order to illustrate the limited coverage of the wall by the anode. The anode 12 may be a metal foil separate from the wall 10 or may be a metal film deposited on a part of the inside surface of the wall 10 by vacuum evaporation or another known technique. As shown in FIG. 3(a), the anode 12 covers the end of the vacuum chamber 14 opposite the end where electrical connections are provided and one-half of the tubular surface of the wall 10, as more clearly shown in FIG. 3(b). As a result of this limited extent of the anode 12, the x-ray radiation 5 has a confined pattern that is limited by the extent of the anode 12.

FIGS. 4(a) and 4(b) are, respectively, a schematic side view and a cross-sectional view taken along the line 4b—4b of FIG. 4(a) and show an alternative arrangement of an x-ray head according to the invention. In the embodiment of FIG. 4(a), the insulating substrate 13 supports two oppositely arranged cathodes 11 so that electrons are produced on opposite sides of the insulating substrate 13. In this embodiment, the anode 12 extends not only over the end of the wall 10 opposite the end where the electrical connections are made but also over all of the tubular surface of the wall 10. As a result, a radial pattern of x-rays, as clearly shown in FIG. 4(b), covers 360° around the longitudinal axis of the substrate 13. In the depicted embodiment, which is not limiting, only two electrical connections are made to the two cathodes which is appropriate if the cathodes are gated field emission cathodes. An additional lead would be required if the cathodes were thermionic cathodes.

Figure 5:
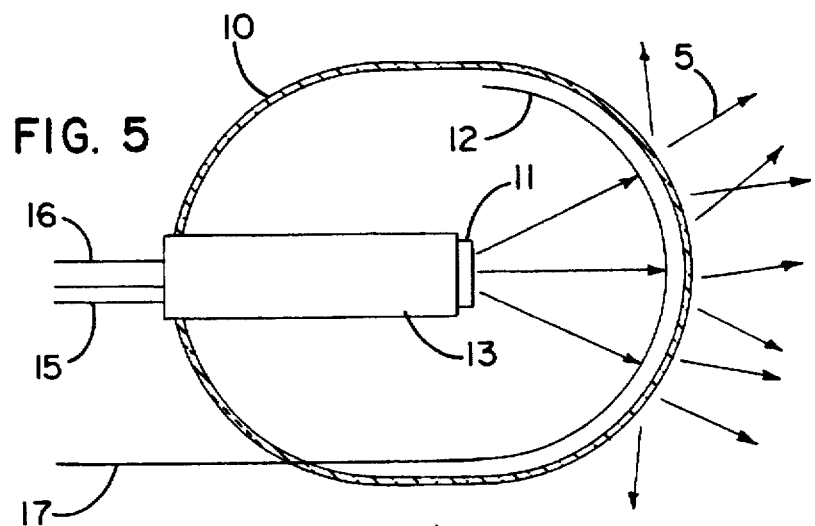
FIG. 5 is a side view of an x-ray head according to an embodiment of the invention.

The x-ray heads illustrated in FIGS. 3(a) and 4(a) produce patterns of x-ray radiation perpendicular to a longitudinal axis of the x-ray heads. A specific x-ray head structure producing x-ray radiation generally parallel to the longitudinal axis of the head, as is produced by the schematic generic x-ray head of FIG. 2, is illustrated in FIG. 5. As in the other figures, the x-ray head of the schematic side view of FIG. 5 includes an outer wall 10, which may be a glass envelope at least partially covered with a plastic material, housing an insulator 13 supporting a cathode 11. In this embodiment, the cathode 11 produces electrons generally parallel to the longitudinal axis of the x-ray head 2 that are accelerated toward the anode 12 which is disposed at the end of the envelope opposite the end where the insulator 13 is supported. In the illustrated embodiment, which is not limiting, a seal is made between the insulator 13 and the outer wall 10 rather than directly to the electrical leads 15 and 16. The anode lead 17 is separate from the other leads and is directly sealed to the outer wall 10. These arrangements are not intended to be limiting but only illustrative since, as shown in other embodiments, the supporting insulator 13 may be transverse to the longitudinal axis of the x-ray and directly supported by the outer wall 10. Alternatively, the cathode leads 15 and 16 may be directly sealed to the outer wall 10 as in the embodiment of FIG. 4(a).

In the illustrative embodiment of FIG. 5, three cathode leads are provided, which is appropriate if the cathode 11 is a thermionic cathode. The electrons produced by the cathode 11 are accelerated toward the anode 12, which may be a metal foil separate from the outer wall 10 or a film of a metal producing x-rays in response to electron impacts. X-rays 5 are scattered over a range of angles relative to the longitudinal axis of the x-ray head but most of the radiation is directed generally parallel to that longitudinal axis.

Figure 6:
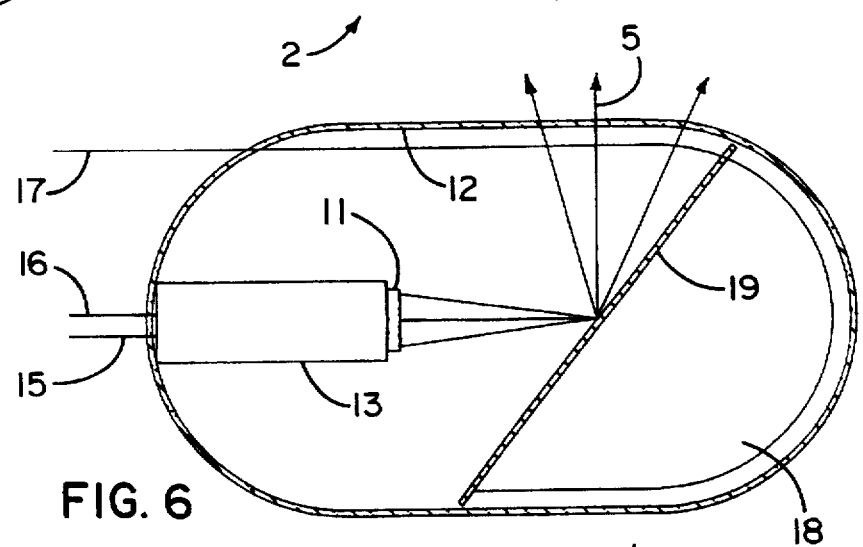
FIG. 6 is a side view of an x-ray head according to an embodiment of the invention.

Still another embodiment of an x-ray head 2 according to the invention is shown in a schematic side view in FIG. 6. The embodiment of FIG. 6 provides yet another means for controlling the pattern of the x-ray radiation produced by the x-ray head. In addition to the elements of x-ray heads already described, the embodiment of FIG. 6 includes a body 18 of a material, such as tungsten, molybdenum, and other known metals, that produces x-rays in response to the impact of electrons of sufficient energy. The body 18 is in electrical contact with the anode 12 and, thus, functions as the anode. The body 18 includes a generally planar surface 19 that is oblique to the longitudinal axis of the x-ray head. Thus, as shown in FIG. 6, x-rays produced in response to electron impacts are directed toward one side of the x-ray head and produce an x-ray beam more limited in angular distribution than the x-ray head embodiments of FIGS. 3(a), 4(a), and 5. Although the anode 12, which provides an electrical connection for the body 18 in the embodiment of FIG. 6, is shown as lying within the pattern of x-ray radiation produced, that conductor 12 is relatively narrow and obscures only a small amount of the x-ray radiation. Alternatively, the anode connection 12 to the body 18 can be made along a path that does not intersect the x-ray radiation from the body 18.

Figure 7A:
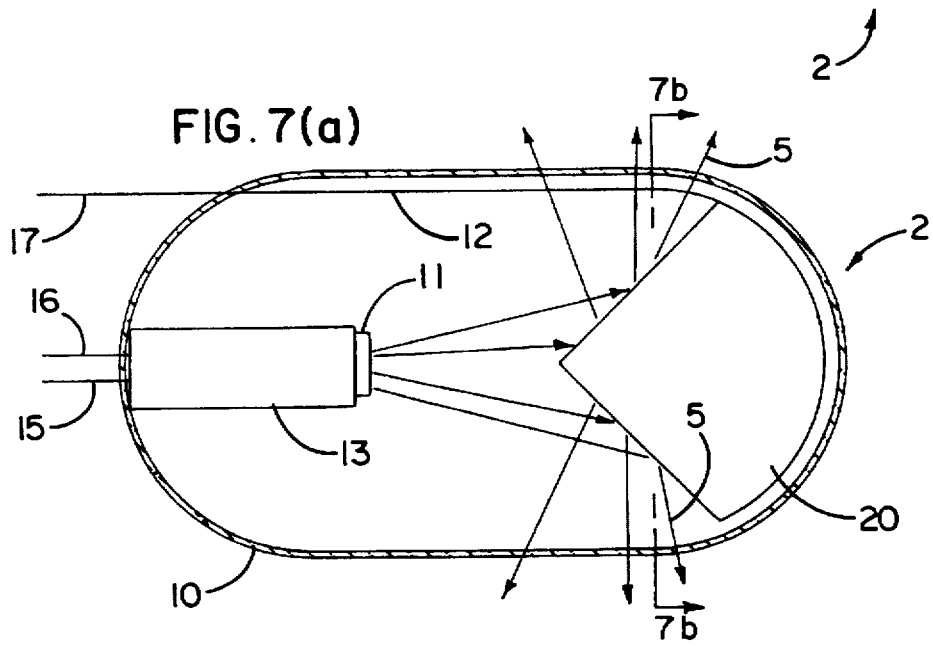
FIGS. 7(a) and 7(b) are, respectively, side and sectional views of an x-ray head according to an embodiment of the invention.
Figure 7B:
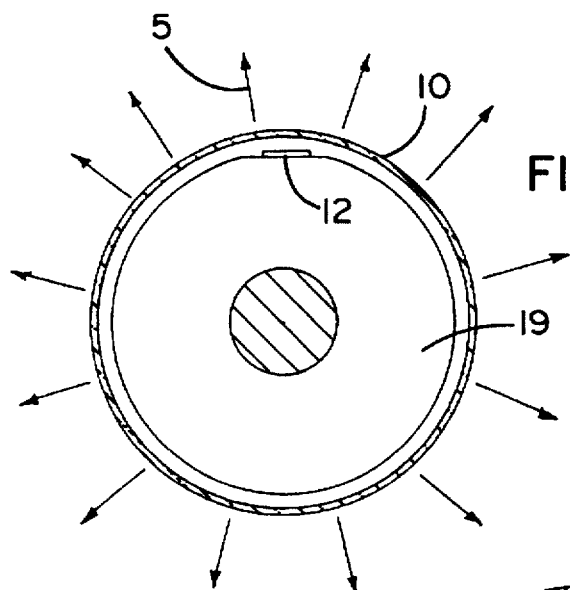

Yet another embodiment of an x-ray head 2 according to the invention producing x-ray radiation in a radial pattern covering 360° is illustrated in FIGS. 7(a) and 7(b). FIG. 7(a) is a side view and FIG. 7(b) is a cross-sectional view taken along line 7b—7b of FIG. 7(a). The embodiment of FIGS. 7(a) and 7(b) differs, in pertinent part, from the embodiment of FIG. 6 in that, in place of the body 18, a conical body 20 of a metal producing x-ray radiation in response to electron bombardment is employed. That conical body 20 produces x-rays in response to energetic electron impacts and is electrically connected by anode 12 to a source of an accelerating voltage. The apex of the conical surface of the body 20 is aligned along the longitudinal axis of the x-ray head and cathode 11 so that the radiation pattern of x-rays is generally radial over a 360° pattern, as illustrated in FIG. 7(b). Otherwise, the x-ray head of FIG. 7(a) is similar to that of the other embodiments and the respective elements of the x-ray head need not be described again in detail. Although the body 20 in FIG. 7(a) is conical and includes a pointed end, the end of the body need not be pointed. Instead, that end can be crowned, i.e., rounded, spreading the pattern of the x-ray radiation somewhat.

Figure 8:
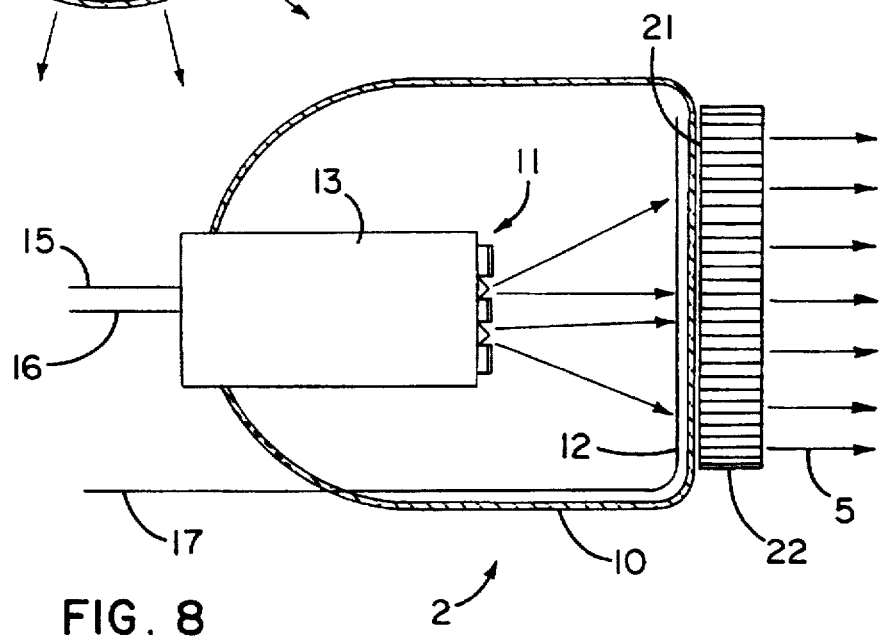
FIG. 8 is a side view of an x-ray head according to an embodiment of the invention.

In each of the embodiments of the x-ray heads illustrated and described with respect to FIGS. 3(a)–7(a), the patterns of x-rays produced are only generally angularly controlled. As a result, x-rays are radiated over a relatively wide angle. FIG. 8 illustrates an embodiment of an x-ray head 2 according to the invention in which a collimated beam of x-rays, i.e., a beam of generally parallel x-rays with controlled angular dispersion, is produced. In this embodiment, the outer wall 10 includes a planar portion 21 opposite the electron producing region of the cathode 11. A portion of the anode 12 is disposed on or adjacent the planar portion 21 of the outer wall 10. On the outside of the wall 10 directly opposite the planar portion 21 of the wall 10 is an x-ray collimator 22. The collimator 22 may be a honeycomb structure of an x-ray absorbing material, such as lead, that absorbs incident x-rays. Most of the x-rays that are generally parallel to the longitudinal axis of the x-ray head pass through one of the plurality of aligned holes of the collimator 22. Those holes are aligned with the longitudinal axis of the cathode. Off axis x-rays strike and are absorbed by the collimator 22. The x-rays that are not absorbed, i.e., that are traveling generally parallel to the longitudinal axis of the x-ray head, produce a collimated x-ray beam having a well controlled pattern that is particularly useful for avoiding unintended irradiation of tissue or a portion of a sample that is intended to be protected from x-ray irradiation.

The foregoing description has been directed to various alternative embodiments of x-ray heads according to the invention. As illustrated, the various x-ray heads may incorporate any of a variety of cathodes producing electrons that are accelerated by a high voltage applied to the anode so that x-rays are produced. In order to achieve the desired miniature x-ray source that is particularly useful in medical applications, any cathode employed must be of very small size. Thus, the most preferred cathodes, which are described in detail below, are solid state cathodes that can be produced in very small sizes yet can generate sufficient electron current to produce x-rays of useful intensity. Examples of field emission, thin film thermionic, and ferroelectric cathodes will be described in turn. These cathodes are typically made using lithographic techniques employed in semiconductor device processing and the cathodes are typically produced as arrays of a large number of small individual cathode elements arranged in a regular geometric pattern. The following description focuses on both individual cathode elements and arrays of those elements.

Figure 9:
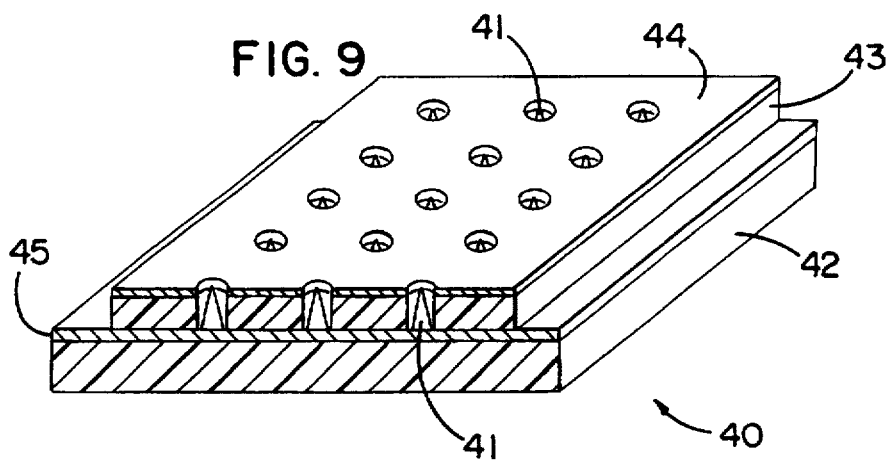
FIG. 9 is a perspective view of a gated field emission cathode that may be used in embodiments of the invention.

A field emission cathode may comprise a gated array of pointed field emission elements or sharp edges or an array of ungated pointed field emission elements or cylinders having edges. FIG. 9 is a schematic, partially sectioned perspective view of a field emission cathode 40 including a gated array of pointed field emission elements 41. Gated field emission arrays are described by Spindt et al in "Field Emitter Arrays For Vacuum Microelectronics", *IEEE Transactions on Electron Devices*, ED-38, 2355 (1991), the disclosure of which is incorporated herein. The field emission phenomenon exploited in these arrays has long been known. When a sufficiently intense electric field, typically 3 to $6 \times 10^9$ V/m, is applied to a material, electrons are torn away from the atoms at the surface of the material. When the material to which the high intensity electric field is applied includes a sharp feature, such as a point or sharp edge, the electric field at that feature is concentrated, i.e., intensified, so that the voltage that must be applied to achieve the threshold electric field for extracting electrons by field emission is reduced. In the invention, electrons extracted from a gated or ungated pointed field emission cathode are accelerated toward and impact on an anode, not shown in FIGS. 9, 12, or 13, resulting in the emission of x-ray radiation from the anode.

The gated field emission cathode of FIG. 9 includes an electrically insulating or conducting substrate 42, an insulating layer 43 disposed on the conducting substrate 42, an conducting electrode 45 disposed on the insulating substrate 42, an insulating layer 43 disposed on the conducting layer 45, an array of electrically conductive pointed field emission elements 41, and a gate electrode 44. The gate electrode 44 includes an opening at each of the field emission elements so that an electric field between the gate electrode 44 and the respective field emission elements can be produced to control the flow of electrons that are emitted from the respective elements in response to an intense electric field. Although only fifteen field emission elements 41 are illustrated in FIG. 9, the number of elements may vary from a small number to a matrix of elements including tens or hundreds of points. The pointed field emission elements 41, shown schematically as conical in the cross-section of FIG. 9, are typically formed from or on the substrate 42 using conventional photolithographic masking and etching techniques, such as are employed in semiconductor device fabrication processes, or chemical vapor deposition. The material of the field emission elements 41 is an electrically conducting material selected from the group including molybdenum, tungsten, carbon in the form of graphite or diamond, silicon, gallium arsenide, and various metals. Although the emitters 41 are shown as conical in most figures, the emitters may have various shapes, such as wedges, including a sharp edge or point. The material of the substrate 42 may be silicon from which the tips 41 are formed or may be a different material, such as glass or quartz, on which the electron emitting elements are formed.

The insulating layer 43 disposed on the substrate 42 surrounds each of the field emission elements 41. The insulating layer 43 may be an oxide of silicon. The insulating film 43 isolates the field emission tips from the gate electrode 44. The gate electrode 44 is a metal film disposed on the insulating film 43 having a matrix of openings, with an opening at each field emission element 41. The spacing between the gate electrode and the respective field emission elements 41 ranges from approximately 0.1 micron to a few microns so that the voltage required to control the electron flow is as low as a few tens of volts. The advantage of a gated field emission cathode is the ability to control the electron flow independent of the accelerating voltage. By applying a controlled voltage to the gate electrode 44, the electron current from the field emission elements 41 to the anode can be limited or modulated and even cut off entirely. The presence of a gate electrode means that the supporting substrate must have separate conductors for the gate electrode 44 and the field emission tips 41, for example, the leads 15 and 16 shown in the embodiments of the invention illustrated in FIGS. 2, 4(a), 6, 7(a), and 8.

Figure 10:
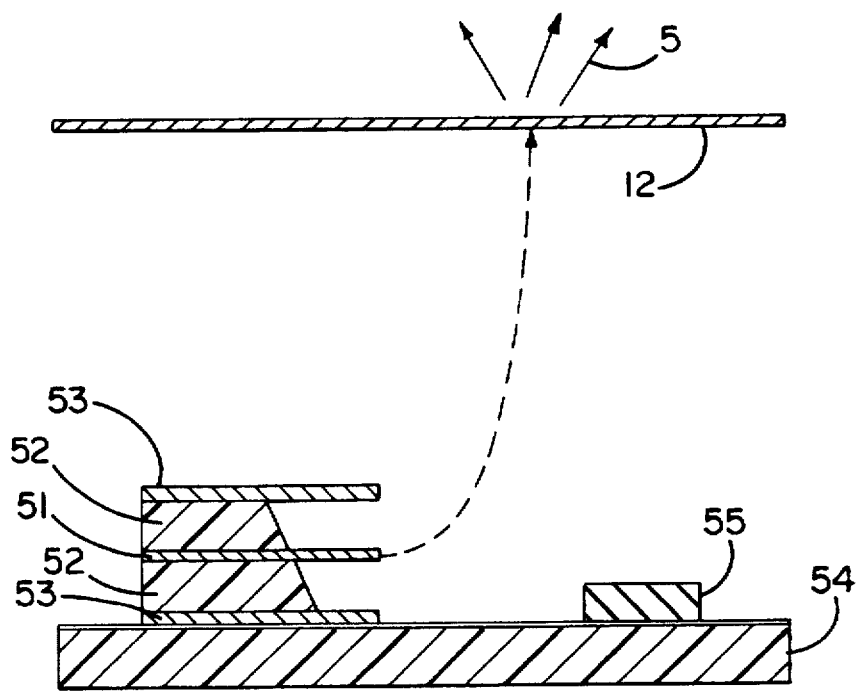
FIG. 10 is a sectional side view of a gated field emission cathode that may be used in embodiments of the invention.
Figure 11:
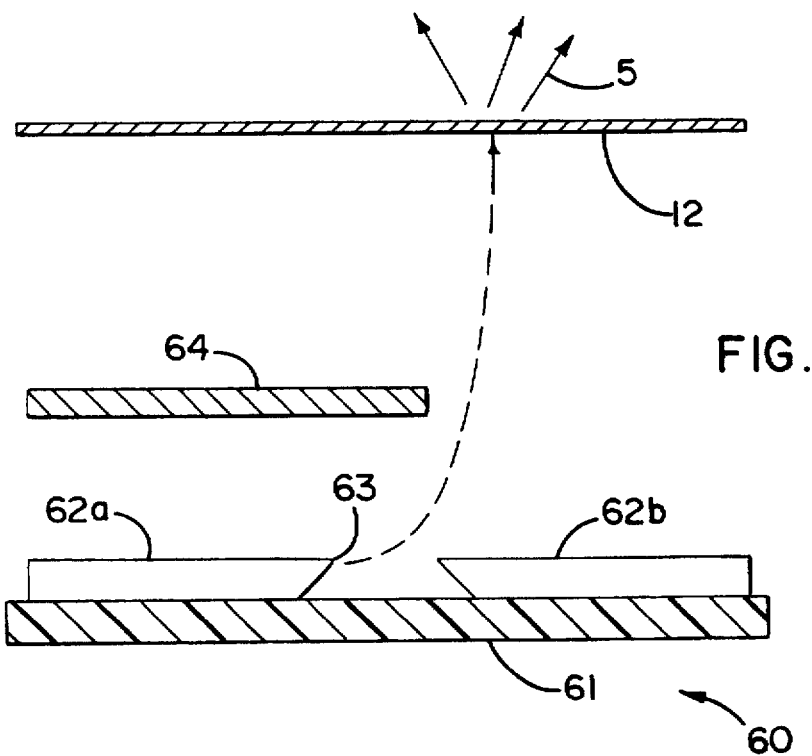
FIG. 11 is a sectional side view of a gated field emission cathode that may be used in embodiments of the invention.

Other examples of field emission cathodes in which electrons are emitted from edges of thin films and semiconductor materials are illustrated in the cross-sectional views of FIGS. 10 and 11. The cathode of FIG. 10 is described in detail by Akinwande et al in "Thin-Film-Edge Emitter Vacuum Microelectronics Devices For Lamp/Backlight Applications", *Technical Digest of 8th International Vacuum Microelectronics Conference*, 1995, pages 418–422, the disclosure of which is incorporated herein. In the gated field emitter 50 of FIG. 10, which is a single example of an emitter that is employed in an array of similar emitters, a thin metal film 51 is sandwiched between two insulators 52. The emitter film may be TiW, Mo, W, or Pt 20 to 30 nanometers thick. The insulators 52 are, in turn, sandwiched by metal gate layers 53 that are positively biased with respect to the emitter layer 51 for emission. This laminated structure is disposed on an insulating substrate 54 and a deflector electrode 55 is disposed on that substrate 54, spaced from and opposite the emitter layer 51. The deflector electrode 55 is negatively biased to deflect the emitted electrons toward the accelerating anode 12 that produces x-rays 5 in response to the incidence of the energetic electrons.

Still another gated field emission cathode 60 is shown in cross-sectional view in FIG. 11. Examples of such gated field emission cathodes producing electrons at an edge of a GaAs film are described by Bandy et al in "Single-Crystal Monolithic Three-Terminal Vacuum Microelectronic Devices Having Maximum Stable Gain At 1 Ghz", *Proceedings, Vacuum Electronics Meeting*, 1993, pages VI-37 to VI-42. The field emission cathode of FIG. 11 includes an insulating substrate 61 on which a GaAs layer 62 is disposed. By appropriate etching, the GaAs layer 62 is divided into parts 62a and 62b with a gap between the two parts of the GaAs layer. The etching forms a relatively sharp edge 63 on layer portion 62a from which electrons are emitted in response to an intense electric field produced by the gate electrode 62b. An airbridge structure includes an electrode 64 that is disposed between the edge 63 and the anode 12 to which a high voltage accelerating potential is applied. That potential accelerates electrons that are extracted from the edge 63. The airbridge structure 64 functions as a electrode deflecting the flow of electrons from the gate electrode 62b. In addition, when the airbridge 64 extends beyond the edge 63, as illustrated in FIG. 11, it protects the edge 63 from ions that can damage the electron emitting edge by unintended sputtering. As with the other gated field emission cathodes, the field emission cathode of FIG. 11 can be made very small by employing conventional technology used in semiconductor manufacturing so that a large array of such field emitting cathode elements can be arranged in an array.

Although gated field emission cathodes are preferable because they permit control of electron flow from a field emission source with a control voltage that is independent of the accelerating voltage, ungated field emission cathodes are also known and can be employed in miniature x-ray heads, such as the x-ray heads 2 previously described. Ungated field emission cathodes employ only one potential difference, the voltage difference between the accelerating electrode, i.e., the anode, and the field emission element. Therefore, it is impossible to adjust the accelerating voltage which determines the energy of the electrons without also affecting the intensity of the electron current. In a gated field emission cathode, the energy of the electrons, which is determined solely by the accelerating voltage of the anode, may be controlled independently of the electron current which is determined by the voltage difference between the gate electrode and the field emission elements.

FIG. 12 is a perspective view of an ungated field emission cathode 70 including an insulating substrate 71 and a plurality of projecting field emission elements 72. In the embodiment of FIG. 12, those elements 72 are pointed projections having a relatively large ratio of length to cross-sectional dimensions and having pointed ends for concentrating the electric field to aid in electron emission.

FIG. 13 is a perspective view of another embodiment of an ungated field emission cathode including an insulating substrate 81 and a single projecting element 82 having a circular cross-section. Although no pointed feature is present on the electron emission element 82, the edge at the circumference of the projection concentrates the accelerating electric field so that electron emission occurs at that edge.

Although the figure indicates that the height of the field emission element 82 is much larger than its diameter, in many practical ungated field emission elements, the element is a relatively thin film of platinum or a laminated structure including platinum in which the cross-sectional dimensions are much larger than the thickness or height dimension. In that structure, a gate can be added provided an insulator is disposed at the periphery of the field emission element 82, separating the element from the electrically conducting gate electrode. The field emission cathode of FIG. 13 and a gated version of it are described by Hsu et al in "Vertical Thin-Film-Edge Field Emitters Fabricated By Chemical Beam Deposition", *Technical Digest of 8th International Vacuum Electronics Conference*, 1995, pages 222–226, the disclosure of which is incorporated herein.

Obviously, an array of electron emitting elements can emit a larger electron current than can a single electron-emitting element and the array can produce an electron flow over a much larger area. Therefore, in general, a field emission cathode including an array of electron emitting elements is preferable to a cathode including only a single such field emission element.

X-ray heads according to the invention can employ lithographically fabricated thin film thermionic cathodes. Examples of thin film thermionic cathodes are described in Sadwick et al, "Microminiature Thermionic Vacuum Tube Diodes", *Technical Digest of the 1993 IEEE International Electron Devices Meeting*, pages 769–772, and Sadwick et al, "Progress in Microminiature Thermionic Vacuum Tube Devices", *Technical Digest of the 1994 IEEE International Electron Devices Meeting*, pages 779–782, the disclosures of which are incorporated herein.

Figure 14A:
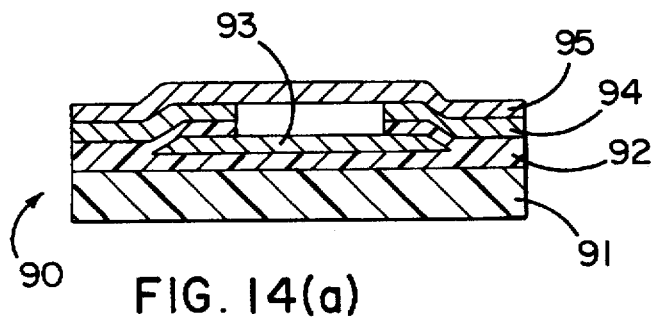
Figure 15:
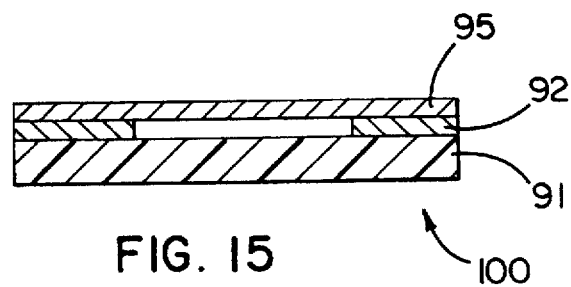
FIG. 15 is a cross-sectional view of an alternative thin film thermionic cathode that may be employed in embodiments of the invention.

Examples of two different thin film thermionic cathode structures are illustrated in cross-sectional views in FIG. 14(a) and 15. FIG. 14(b) is a perspective view of the thermionic cathode illustrated in FIG. 14(a). These cathodes were developed for use in vacuum tube-like solid state structures but, in the invention, they are employed as electron sources for generating x-rays. These thermionic cathode structures are prepared using techniques conventionally employed in semiconductor device manufacturing processes.

The thermionic cathode 90 of FIGS. 14(a) and 14(b) employs an airbridge structure in which a metal layer is partly supported by a sacrificial layer that is removed, for example, by chemical etching, after the metal layer of the airbridge is deposited. The thermionic cathode structure 90 of FIGS. 14(a) and 14(b) includes an electrically insulating substrate 91 that can withstand a relatively high temperature, such as silicon, and has an insulating film 92, such as silicon nitride or a silicon oxide, deposited on it. A metal layer 93 of a material that can withstand relatively high temperatures, such as platinum, is disposed on and partly embedded in the insulating layer 92. When the thermionic cathode is used as an analog of a vacuum tube diode, the metal layer 93 functions as an anode or plate. However, in the present invention in which the cathode is a source of electrons for producing x-rays, the metal layer 93 functions as a grid or gate electrode that controls electron flow from the cathode. The metal layer 93 must withstand the high temperatures generated by the heated conductor of the thermionic structure. An electrically conducting material that is easily contacted, such as aluminum, is present in a layer 94 between the insulator 92 and a metal film 95 that forms the airbridge structure and functions as the high temperature filament of the cathode structure. The film 95 is separated by a void space from the metal 93 as an airbridge. Examples of metals suitable for the film 95 are tungsten and molybdenum. Although not illustrated in FIGS. 14(a) and 14(b), preferably an electron-emitting coating, such as mixed oxides of alkaline earth elements that are well known in the vacuum tube art, is present on the surface of the metal film 95. That coating aids in the emission of electrons when the metal film 95 is heated by current flowing through it. Depending upon the potential of the metal layer 93 relative to the metal film 95, emitted electrons may be attracted to or repelled by the metal layer 93 so that that layer functions as a gate electrode.

FIG. 15 is a cross-sectional view of another, simpler embodiment of a thermionic cathode 100. This thermionic cathode is sometimes referred to as a trench structure and lacks a metal layer corresponding to the gate electrode 93 of the structure of FIG. 14(a). Instead, the insulating substrate 91 supports an insulating layer 92 on which the metal film 95 forming the analog of a filament is present. Part of the metal film 95 is separated by a void space from the substrate 91 as in the thermionic cathode structure 90. An gate electrode is fabricated on the same plane as the cathode 95, separating by a few microns. However, it is possible to regulate electron current independent of the accelerating voltage applied to an anode, not shown in FIGS. 14(a) and 15, by controlling the current flowing through the metal film 95. The current flow controls the temperature of the metal film 95 and, thereby, the rate at which electrons are emitted. Thus, the electron current may be varied independent of the accelerating voltage. In FIGS. 14(a), 14(b), and 15, as in other depictions of cathodes, for simplicity, wiring connections are not illustrated. However, each of the thermionic cathode structures requires two leads for providing a current flow through the metal film 95 that is heated in order to produce electrons. In addition, in the gated structure of FIG. 14(a), an additional lead is required to apply a potential to the gate electrode. Thus, as in the embodiments of the invention illustrated in FIGS. 3(a) and 5, a thermionic cathode will typically require a three lead connection. As with field emission cathodes, the thermionic cathodes are typically arrays of the individual elements of FIGS. 14(a) and 15.

Figure 16A:
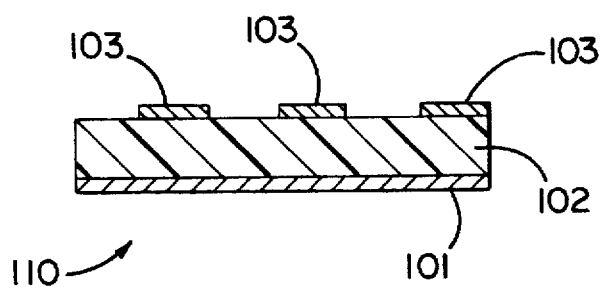
FIGS. 16(a) and 16(b) are, respectively, cross-sectional and plan views of a ferroelectric cathode that may be employed in embodiments of the invention.
Figure 16B:
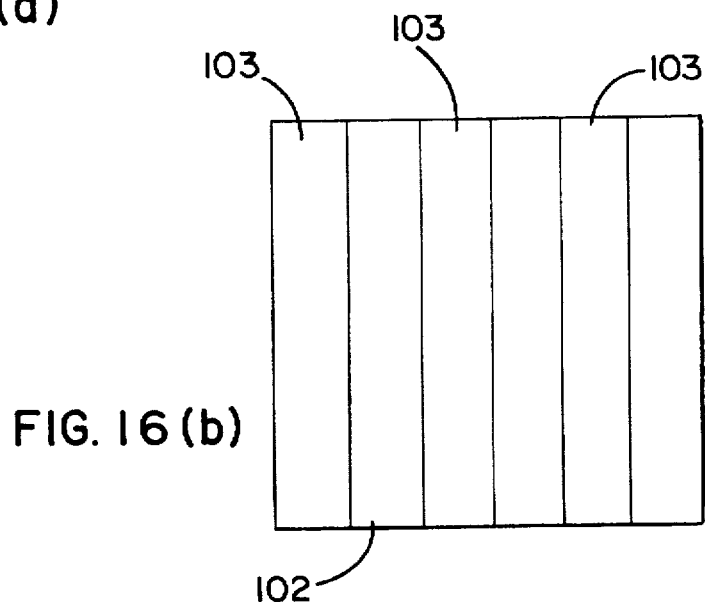

Still another kind of cathode structure that may be used in embodiments of the invention is a ferroelectric cathode. A ferroelectric cathode 110 is shown in a cross-sectional view and in a plan view in FIGS. 16(a) and 16(b), respectively. The ferroelectric cathode 110 includes an insulating substrate 102 of a particular material, for example, lead lanthanum zirconate-titanate (PLZT), and lead zirconate-titanate (PZT). Art electrode 101 covers the rear surface of the substrate and electrodes 103 in spaced apart parallel stripes are disposed on the opposite surface of the substrate 102. The electrodes may be platinum or another metal. The electrode on the rear surface of the substrate need not be a high temperature metal and may be aluminum or gold, for example. The dimensions of these cathodes are similar to the other miniature cathodes already described. For example, the substrate may have a thickness of only about 100 microns for PLZT and under 10 microns for PZT. The stripe-shaped electrodes illustrated in FIG. 16(b) are not limiting and may be replaced by square electrodes or rectangular electrodes of different aspect ratios. Ferroelectric cathodes are described in further detail by Auchiello et al in "Low Voltage Electron Emission From $Pb(Zr_xTi_{1-x})O_3$-Based Thin Film Cathodes", *Applied Physics Letters*, Volume 66, 1995, pages 2183–2186, the disclosure of which is incorporated herein. Through a mechanism not fully understood, electrons are emitted from the front surface of the substrate 102 adjacent the electrodes 103 when a pulsed voltage of approximately 400 volts for PLZT cathodes and about 40 volts for PZT cathodes is applied between the electrodes 103 and 101. As with other cathode elements, the ferroelectric cathode of FIG. 16(a) is only an example of one cathode element. In application to the invention, an array of such cathode elements is present on a substrate to produce a current density sufficient to generate x-rays of useful intensity.

An important common feature of all of the cathodes described is the ability to fabricate them using photolithography, etching, and thin film deposition techniques that are commonly used in the semiconductor arts. These techniques permit the formation of each of the different types of cathodes with dimensions of microns to tens of microns. Thus, arrays of each of the different types of cathodes can readily be made so that the entire cathode structure including a large number of cathode elements has outer dimensions of millimeters to tens of millimeters. Thus, a microminiature x-ray source can readily be made according to the invention. In addition, because such a large number of cathodes are included in the array, even if the electron current from each element is insufficient to produce an x-ray radiation of adequate intensity for analytical, diagnostic, or therapeutic purposes, the total electron current from all of the cathode elements in the array is sufficient to produce the desired x-ray radiation intensity.

As in all x-ray equipment, it is important to maintain a stable vacuum within which the electrons are generated and accelerated from the cathode to the anode. For example, in a gated field emission array cathode structure, a vacuum of $10^{-9}$ to $10^{-6}$ Torr is required to ensure steady electron emission. Thermionic cathodes can tolerate poorer vacuum levels, for example, $10^{-6}$ Torr. These levels of vacuum can be achieved by active gettering of residual gases within the vacuum chamber 14.

With the miniature x-ray source according to the invention, x-ray images that would have been previously difficult to form may be simply made. For example, images of small tissue samples may be obtained. Art x-ray source according to the invention may be placed in the mouth of a patient and x-ray film placed outside the mouth so that an image of the mandibular joint close to the ear can be made, notwithstanding the presence of bone and tissue in that area.

The x-ray source has been particularly described with respect to medical applications. However, the x-rays produced by the source can also be used for various scientific experiments, such as x-ray fluorescence analysis, x-ray absorption measurements, x-ray radiography, and x-ray tomography, where the x-ray head may be placed in close proximity to the sample being analyzed and to a means of detecting x-rays that have passed through a sample, such as photographic film.

Although the invention has been described with respect to certain preferred embodiments, those of skill in the art will recognize various additions and modifications from the foregoing description within the spirit of the invention. The invention is not restricted to the particular constructions described and illustrated but is limited only by the scope of the following claims.

We claim:

1. An x-ray source including:
   a head comprising an evacuated envelope having an outer wall and containing an anode made of a metal producing x-rays in response to the impact of electrons, a cathode including an array of cathode elements respectively producing electrons accelerated toward the anode in response to an electric field between the anode and the cathode elements, the cathode not exceeding ten centimeters in maximum dimension so that the x-ray source can be inserted into a cavity of the human body, the anode being spaced sufficiently far from the cathode for applying an accelerating voltage between the cathode and the anode without voltage break-down and producing x-rays of wavelengths suitable for diagnosis and treatment of a human, and a gate electrode for controlling the flow of electrons from the cathode to the anode; and
   respective electrical leads extending from the anode and the cathode and out of the envelope.

2. The x-ray source of claim 1 wherein each of the cathode elements is a field emission cathode producing electrons in response to an electric field.

3. The x-ray source of claim 1 wherein each of the cathode elements is a thin film thermionic cathode element including a metal film directly heated by a current flowing through the metal film for emitting electrons.

4. The x-ray source of claim 1 wherein the anode includes a metal body having a generally planar surface directed toward the cathode and oblique to a direction along which electrons are emitted from the cathode.

5. The x-ray source of claim 1 wherein each of the cathode elements is a ferroelectric cathode element producing electrons in response to a pulsed electrical signal.

6. The x-ray source of claim 1 wherein the anode is disposed opposite only part of the envelope.

7. The x-ray source of claim 1 wherein the anode is a metal foil.

8. The x-ray source of claim 1 wherein the anode is a metal film deposited on the envelope.

9. The x-ray source of claim 1 wherein the anode includes a metal body having a generally conical surface pointed toward the cathode and aligned with a direction along which the cathode emits electrons.

10. The x-ray source of claim 1 wherein the evacuated envelope has an outer wall including a generally planar portion on which the anode is disposed and a collimating element disposed adjacent the planar portion of the envelope for collimating x-ray radiation produced at the anode.

11. The x-ray source of claim 10 wherein the collimating element is a metal that absorbs x-rays and includes a plurality of aligned holes for passage of x-rays that are not incident on the collimating element.

12. The x-ray source of claim 10 wherein the collimating element is disposed outside the envelope adjacent the planar portion of the envelope.

* * * * *